Figure 1:
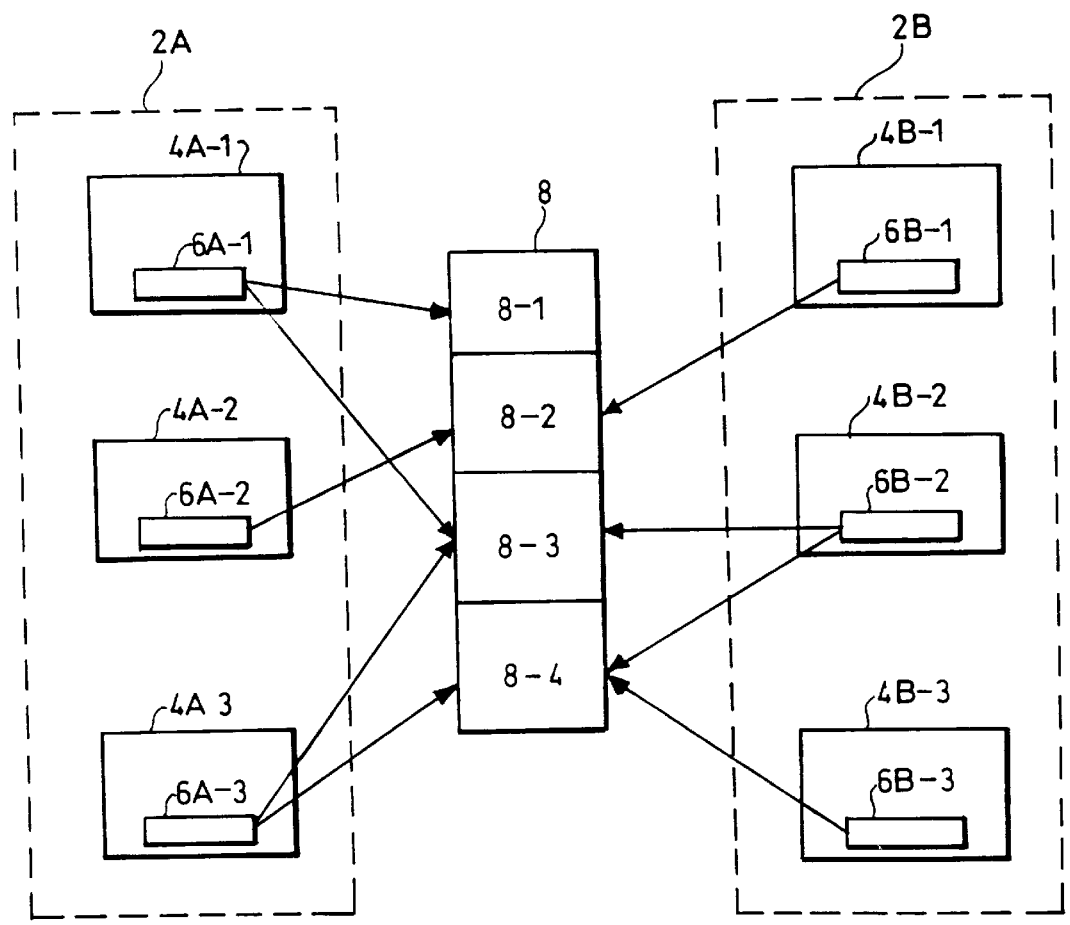

United States Patent
Blatchford

[19]

[11] Patent Number: 5,972,035
[45] Date of Patent: Oct. 26, 1999

[54] SPECIFICATION OF AN ARTIFICIAL LIMB

[75] Inventor: Brian Stephen Blatchford, Farnham, United Kingdom

[73] Assignee: Chas. A. Blatchford & Sons, Limited, United Kingdom

[21] Appl. No.: 08/842,557

[22] Filed: Apr. 15, 1997

[30] Foreign Application Priority Data

Apr. 15, 1996 [GB] United Kingdom ............ 9607749

[51] Int. Cl.[6] .................................................. A61F 2/76
[52] U.S. Cl. ........................... 623/27; 623/57; 623/901
[58] Field of Search ....................... 623/27, 38, 901, 623/57; 364/468.09, 468.1

[56] References Cited

U.S. PATENT DOCUMENTS 5,225,987 7/1993 Thompson ............... 364/468.09 X
5,442,563 8/1995 Lee ............................... 364/468.1

FOREIGN PATENT DOCUMENTS 8902888 6/1991 Netherlands ..................... 623/901

*Primary Examiner*—David H. Willse
*Attorney, Agent, or Firm*—Fish & Richardson P.C.

[57] ABSTRACT

A method of constructing an artificial limb from individual components comprising providing a plurality of logical unit tables (2A, 2B) arranged to contain data related to a respective class of the components, providing a plurality of component records (4A, 4B) located in at least one of the logical unit tables (2A, 2B) arranged to hold data related to a respective plurality of components of the same class providing an interface field (6A, 6B) located in each respective component record (4A, 4B) arranged to hold data related to an interface of the component to which the component record relates, selecting a component record (4A, 4B) generating a list of compatible component records from a logical unit table (2A, 2B) other than the logical unit table containing the selected component record (4A, 4B), which are compatible with the selected component taking account of the information contained in the interface fields (6A, 6B) of the selected component record (4A, 4B) and the component records in the other logical unit table (2A, 2B), and constructing an artificial limb including the component to which the selected component relates and at least one component to which one of the compatible component records relates.

17 Claims, 2 Drawing Sheets

SPECIFICATION OF AN ARTIFICIAL LIMB

The present invention relates to a method of specifying the components of an artificial limb, a method of constructing such an artificial limb and to apparatus for specifying the components.

An artificial limb comprises many components which must fit together correctly to ensure correct functioning of the limb. Components for a complete limb can be sourced from one or more manufacturers. Each manufacturer's product range can cover a diverse range of options and can be connected to other manufacturer's products. Thus, it can be a complicated and skilled job to select components which permit a limb to perform the required functions and which fit correctly together. Furthermore it is difficult accurately to estimate the cost of a complete limb prior to construction since errors in its specification may not be realised until construction is attempted.

It is an object of the present invention to provide an improved method and means of specifying the components which make up an artificial limb.

According to the present invention, a method of constructing an artificial limb from individual components comprises providing a plurality of logical unit tables arranged to contain data related to a respective class of the components, providing a plurality of component records located in at least one of the logical unit tables arranged to hold data related to a respective plurality of components of the same class, providing an interface field located in each respective component record arranged to hold data related to an interface of the component to which the component record relates, selecting a component record, generating a list of compatible component records from a logical unit table other than the logical unit table containing the selected component record, which are compatible with the selected component taking account of the information contained in the interface fields of the selected component record and the component records in the other logical unit table, and constructing an artificial limb including the component to which the selected component record relates and at least one component to which one of the compatible component records relates.

The classes of components will in an above-knee prosthesis, typically be a socket, an alignment mechanism, a shin/knee component, an ankle component, a foot and a cosmesis. Once a component record has been selected which might for example be from the logical unit related to the shin component class, a list of compatible component records relating to the class of ankle components may be generated. Since the information held in the interface fields relating to the particular shin component has been taken into account when generating the list, the list will only include component records relating to ankle components which can be connected to the chosen shin component. For other amputation levels different classes of components may be selected.

Preferably a further component record is selected from the generated list and a further list of compatible component records is generated based on the further component record. This may for example be a list of feet that can be connected to the chosen ankle component. By repeating this process, to select a component from each class i.e. from each logical unit table, a complete limb may be specified and then constructed in accordance with the present invention.

According to a second aspect of the invention, a method of specifying the components of an artificial limb comprises providing a plurality of logical unit tables arranged to contain data related to a respective class of the components, providing a plurality of component records located in at least one of the logical unit tables arranged to hold data related to a respective plurality of components of the same class, providing an interface field located in each respective component record arranged to hold data related to an interface of the component to which the component record relates, selecting a first component record, generating a first list of compatible component records from a logical unit table other than the logical unit table containing the selected first component record, which are compatible with the first selected component taking account of the information contained in the interface fields of the first selected component record and the component records in the other logical unit table.

Preferably the method includes selecting a further component record from the first list, generating a further list of compatible component records based on the further component record and repeating the selection and list generation steps until the required number of components have been specified.

Typically the method includes providing an interface table and further includes arranging each interface field to include a pointer to the interface table. Advantageously, the interface table may include details of any components which may be required to adapt a component to fit to another component so that the generated list may also include a list of components associated with the components related to the listed component records. In this way, a user of the invention, may be provided with a complete parts list for the limb including any additional components which fall outside the classes of components selected for entry into the logical unit tables. This is particularly advantageous since the selection of appropriate adaptors is a particularly skilled task.

According to a third aspect of the invention, apparatus for specifying the components of an artificial limb comprises a plurality of logical unit tables arranged to contain data related to a respective class of the components, a plurality of component records located in at least one of the logical unit tables arranged to hold data related to a respective plurality of components of the same class, an interface field located in each respective component record arranged to hold data related to an interface of the component to which the component record relates, user input means for selecting a component record, and output means for outputting a list of compatible component records from a logical unit table other than the logical unit table containing the selected component record, which are compatible with the selected component taking account of the information contained in the interface fields of the selected component record and the component records in the other logical unit table.

Typically the invention will be implemented on a computer system including storage means for storing the logical unit tables and any associated data such as the interface table. Typically a component such as a shin/knee component will have three interface tables associated with it, one for its upper interface for example with an alignment mechanism, one for its lower interface for example with an ankle component, and one between the shin/knee and a cosmesis. The table relating to the interface between the ankle and the shin is preferably a single table which is pointed to by the interface fields of both the shin/knee logical unit table and the ankle logical unit table.

The invention will now be described by way of example with reference to

Figure 2:
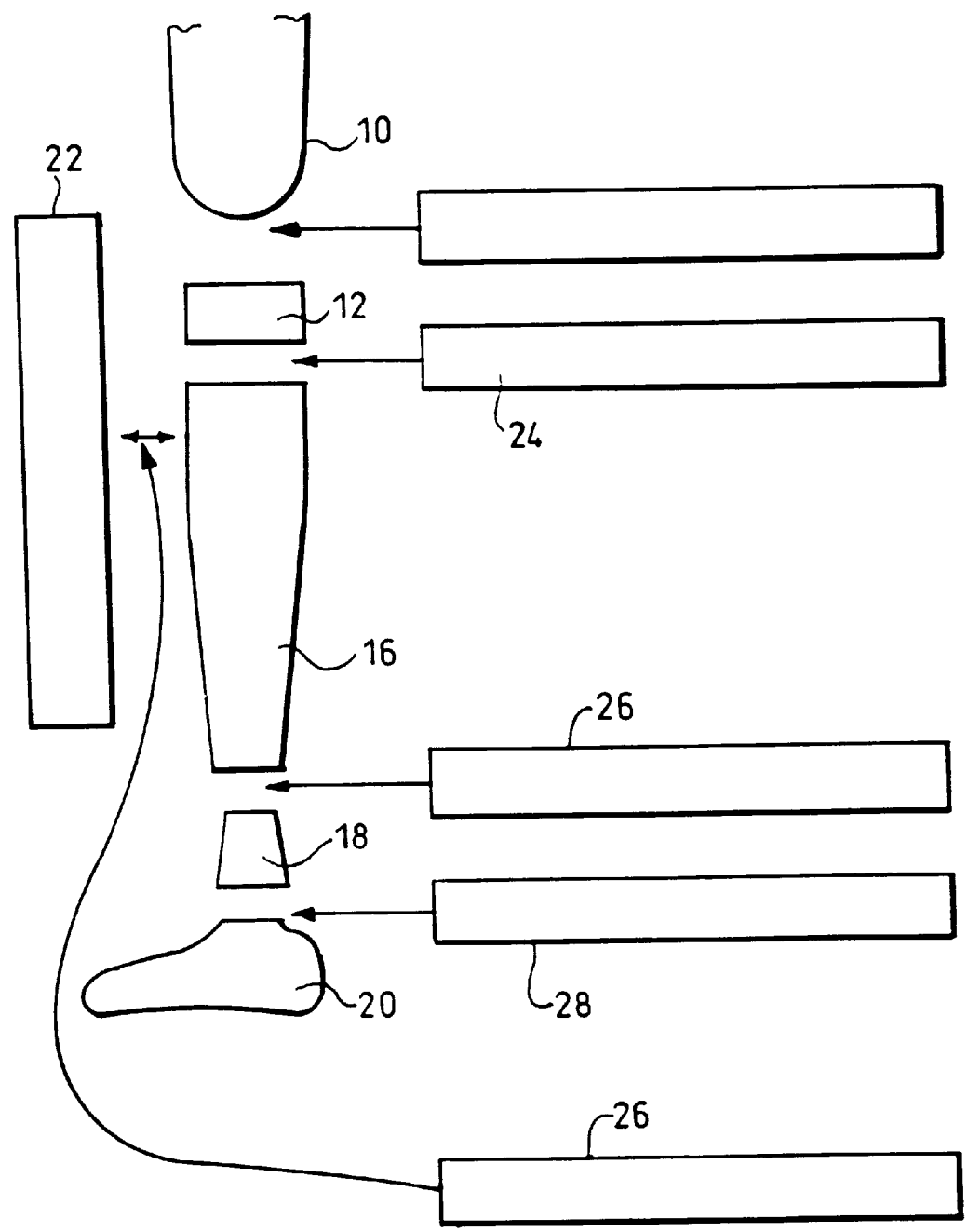

FIG. 1 which is a schematic block diagram of an apparatus constructed in accordance with the invention; and FIG. 2 which is a schematic diagram of the logical units of an above-knee prosthesis showing interface tables in accordance with the invention.

With reference to FIG. 1, logical unit tables 2A, 2B hold respective component records 4A-1, 4A-2, 4A-3, 4B-1, 4B-2, 4B-3 which in turn each hold interface fields 6A-1, to 6B-3. Each interface field contains a pointer to at least one entry in an interface table 8.

Each logical unit table 2 contains components records 4 relating to a particular respective class of components of a limb, for example a foot component and an ankle component. Each component record 4 represents a particular example of that class of component perhaps from a different product range of the same manufacturer or from a different manufacturer.

The interface table 8 contains in each entry, information relating to each possible physical interconnection or interface between the two classes of components. Where a class of component has more than one interface for example a knee/shin component which must interconnect with an alignment mechanism at its upper interface and with an ankle component at its lower interface, a separate interface table is provided for each physical interface.

Each entry in the interface table represents a different type of interconnection between components.

Taking component record 4A-1 as an example, it will be seen that its interface field 6A-1 points to two entries in the table 8, namely entries 8-1 and 8-3. This component record therefore relates to a component having two possible methods of interconnection with a component of the class represented by logical unit 2B. Looking at logical unit 2B however it is clear that no component records of this class of components point to interface table entry 8-1. Thus there are no components of the class represented by logical unit 2B which can be interconnected using the interface type represented by interface table entry 8-1 to connect with the component represented by component record 4A-1. From the diagram it is clear that the only component which can be used with the component represented by component record 4A-1 is the component represented by component record 4B-2, since these may be interconnected using the interface type represented by interface table entry 8-3.

In some circumstances it will be necessary to fit adaptor kits to components to allow them to connect to other components. In this case the corresponding entry in interface table 8 contains details of the necessary adaptor kit. If the table contains a null entry then the two components may be fitted directly together.

Once one of the components has been selected by a user from the logical unit table, for example component record 4A-3, the apparatus in accordance with the invention generates a list of possible component records which may be chosen from the logical unit table 2B. In this example the list will include the components represented by component records 4B-2 (via the interfaces represented either by interface table entry 8-3 or 8-4) and the component represented by component record 4B-3. Since for component 4B-2 there is a choice of interface methods it is likely that one of these will involve the use of an adaptor kit. In this case then the list will include three entries, two of the component represented by component record 4B-2 (one including an adaptor kit) and an entry relating to the component represented by component record 4B-3. Similarly the component represented by the selected component record has two possible interfaces (entries 8-3 and 8-4) one of which also is likely to involve the use of an adaptor kit.

The user having been presented with the list of components which may be connected to the first selected component, may select one of these listed components to generate a further list of components. For example having selected a shin and been presented with a list of possible ankles, the user may then select one of the ankles to determine which feet may be connected to that ankle. In this way a complete list of components to specify a whole limb may be produced.

Conceptually, each logical unit (comprising a class of components and its associated interface information) maps onto one or more components which perform the function required of a particular logical unit (e.g. a foot or ankle). A plurality of components may be required for a complete logical unit where an interface or adaptor kit is required. In some cases, the interface may be integral with the component. In this case, the component record will reflect a choice of component (chosen to select the appropriate interface). Thus, the underlying part number for a component may change according to interface requirements.

The division of an above knee prosthesis into several logical units each having a logical unit database is shown in FIG. 2.

The prosthesis is divided into six logical units namely a socket 10, an alignment mechanism 12, a shin/knee component 16, an ankle component 18, a foot component 20 and a cosmesis 22. Information about each possible component for each logical unit is held in a separate information table which in particular may hold a price, a part number, a maximum weight limit, approval information, the name of the manufacturer and a common name of the component which will be recognised by the user. Since a component may be included in several component records, storage space is saved by storing the detailed information of the information table, once only for a particular component.

Taking as an example, the shin/knee 16, this has three interfaces represented by tables 22, 24 and 26. These are the tables numbered 8 in FIG. 1. Thus a component record for a shin/knee component will have pointers to three interface tables since a knee component has three interfaces, namely those between the knee and the alignment mechanism, the knee and the knee and the ankle and the cosmesis.

The model described above sometimes must be varied to accommodate peculiarities in the product ranges provided by manufacturers. For example, the fixings of the knee/shin component may vary depending on whether a continuous or discontinuous cosmesis is used. In this case, the interface table holds two entries which are both presented as options in the output list. The two entries relate to the components which must be used to interconnect the shin/knee component depending on which type of cosmesis is to be used. Similarly, in certain product ranges, there is no interface between the ankle and shin components since the shin component connects directly between the foot and the alignment mechanism and includes an ankle component. In this case, the interface field for that shin/knee component record points directly to entries in the ankle-foot interface table 28 which entries will in turn, be pointed to by interface fields from compatible feet.

In summary, the invention provides a tool which greatly simplifies the selection of appropriate components for the construction of an artificial limb by presenting a user with a list of compatible components by taking account of the characteristics of each component. The list is refined by the user making selections from a presented list in order to cause the generation of one or more further lists.

I claim:

1. A method of constructing an artificial limb from individual components comprising providing a plurality of logical unit tables arranged to contain data related to a respective class of the components, providing a plurality of component records located in at least one of the logical unit tables arranged to hold data related to a respective plurality of components of the same class, providing an interface field located in each respective component record arranged to hold data related to an interface of the component to which the component record relates, selecting a component record, generating a list of compatible component records from a logical unit table other than the logical unit table containing the selected component record, which are compatible with the selected component taking account of the information contained in the interface fields of the selected component record and the component records in the other logical unit table, and constructing an artificial limb including the component to which the selected component record relates and at least one component to which one of the compatible component records relates.

2. A method according to claim 1, including the additional steps of selecting a further component record from the generated list of compatible component records and generating a further list of compatible component records from a logical unit table other than the logical unit table containing the selected component record and the selected further component record, which are compatible with the selected further component taking account of the information contained in the interface fields of the selected further component record and the component records in the generated list.

3. A method according to claim 1, including providing an interface table, and providing an interface pointer in at least one of the interface fields operable to point to the interface table.

4. A method according to claim 3 including providing at least one interface field with a plurality of the interface pointers.

5. A method according to claim 3, including arranging for interface pointers associated with (component records from different logical unit tables to point to the same interface table.

6. A method of specifying the components of an artificial limb comprising providing a plurality of logical unit tables arranged to contain data related to a respective class of the components, providing a plurality of component records located in at least one of the logical unit tables arranged to hold data related to a respective plurality of components of the same class, providing an interface field located in each respective component record arranged to hold data related to an interface of the component to which the component record relates, selecting a first component record, generating a first list of compatible component records from a logical unit table other than the logical unit table containing the selected first component record, which are compatible with the first selected component taking account of the information contained in the interface fields of the first selected component record and the component records in the other logical unit table.

7. Apparatus for specifying the components of an artificial limb comprising a plurality of logical unit tables arranged to contain data related to a respective class of the components, a plurality of component records located in at least one of the logical unit tables arranged to hold data related to a respective plurality of components of the same class, an interface field located in each respective component record arranged to hold data related to an interface of the component to which the component record relates, user input means for selecting a component record, and output means for outputting a list of compatible component records from a logical unit table other than the logical unit table containing the selected component record, which are compatible with the selected component taking account of the information contained in the interface fields of the selected component record and the component records in the other logical unit table.

8. Apparatus according to claim 7 wherein the user input means are operable to select a further component record from the list of compatible component records and wherein the output means are operable to generate a further list of compatible component records from a logical unit table other than the logical unit table containing the selected component record and the selected further component record, which are compatible with the selected further component taking account of the information contained in the interface fields of the selected further component record and the list of compatible component records.

9. Apparatus according to claim 7, including an interface table and in which at least one of the interface fields includes an interface pointer operable to point to the interface table.

10. Apparatus according to claim 9, wherein at least one interface field includes a plurality of the interface pointers.

11. Apparatus according to claim 9, wherein a plurality of interface pointers associated with component records from respective different logical unit tables are arranged to point to the same interface table.

12. A computer system including a plurality of logical unit tables arranged to contain data related to a respective class of individual components of an artificial limb, a plurality of component records located in at least one of the logical unit tables arranged to hold interface data related to an interface of the component to which the component record relates, the computer system being operable to select a component record and to generate a list of compatible component records from a logical unit table other than the logical unit table containing the selected component record, which are compatible with the selected component taking account of the interface data of the selected component record and the interface data of the component records in the other logical unit table.

13. A computer system according to claim 12, further operable to select a further component record from the generated list of compatible component records and to generate a further list of compatible component records from a logical unit table other than the logical unit table containing the selected component record and the selected further component record, which are compatible with the selected further component taking account of the interface data of the selected further component record and the interface data of the component records in the generated list.

14. A computer system according to claim 12, including an interface table, and an interface pointer in at least one of the component records operable to point to the interface table.

15. A computer system according to claim 14 including at least one component record with a plurality of the interface pointers.

16. A computer system according to claim 14 operable to arrange for interface pointers associated with component records from different logical unit tables to point to the same interface table.

17. A computer system for specifying the components of an artificial limb including a plurality of logical unit tables arranged to contain data related to a respective class of the components, a plurality of component records located in at least one of the logical unit tables arranged to hold data related to a respective plurality of components of the same class, an interface field located in each respective component record arranged to hold data related to an interface of the component to which the component record relates, and arranged to select a first component record and to generate a first list of compatible component records from a logical unit table other than the logical unit table containing the selected first component record, which are compatible with the first selected component taking account of the information contained in the interface fields of the first selected component record and the component records in the other logical unit table.

* * * * *